(12) United States Patent  (10) Patent No.: US 7,488,321 B2
Lin  (45) Date of Patent: Feb. 10, 2009

(54) BONE FIXATION DEVICE

(75) Inventor: Chih-I Lin, Taipei (TW)

(73) Assignee: A-Spine Holding Group Corp., Tortola (VG)

( * ) Notice: Subject to any disclaimer, the term of this patent is extended or adjusted under 35 U.S.C. 154(b) by 816 days.

(21) Appl. No.: 10/961,026

(22) Filed: Oct. 12, 2004

(65) Prior Publication Data

US 2005/0261689 A1 Nov. 24, 2005

(30) Foreign Application Priority Data

May 20, 2004 (TW) .............................. 93114307 A

(51) Int. Cl.
A61B 17/56 (2006.01)

(52) U.S. Cl. ....................................... 606/71

(58) Field of Classification Search ............ 606/69–71, 606/151, 157, 280–291; 24/573.09, DIG. 31, 24/DIG. 44, DIG. 45
See application file for complete search history.

(56) References Cited

U.S. PATENT DOCUMENTS

| 2,495,667 | A | * | 1/1950 | Vizner | 24/593.1 |
| 2,532,162 | A | * | 11/1950 | Goss | 248/477 |
| 4,201,215 | A | * | 5/1980 | Crossett et al. | 606/216 |
| 5,457,859 | A | * | 10/1995 | Kacprowicz et al. | 24/573.09 |
| 6,235,059 | B1 | * | 5/2001 | Benezech et al. | 623/17.16 |
| 6,652,525 | B1 | * | 11/2003 | Assaker et al. | 606/61 |
| 2003/0187506 | A1 | * | 10/2003 | Ross et al. | 623/17.13 |
| 2005/0177160 | A1 | * | 8/2005 | Baynham et al. | 606/69 |
| 2005/0192576 | A1 | * | 9/2005 | Michelson | 606/61 |

* cited by examiner

Primary Examiner—Eduardo C Robert
Assistant Examiner—Michael J Araj
(74) Attorney, Agent, or Firm—Bacon & Thomas PLLC

(57) ABSTRACT

A bone fixation device includes: a bone plate having a plurality of through holes; and one or a plurality of bone screws; wherein the bone plate is provided with a slide track on a surface thereof, and the bone plate is further provided with one or a plurality of sliding covers slidablely connected to the slide track and capable of covering the through holes. The bone screws has a threaded body, a head and a neck therebetween, wherein a thread of the threaded body close to the neck has an angle slightly inclined towards to the threaded body.

3 Claims, 4 Drawing Sheets

BONE FIXATION DEVICE

BACKGROUND OF THE INVENTION

1. Field of the Invention

The present invention relates to a bone fixation device and, more particularly, to a bone fixation device for vertebrae which includes a sliding cover and bone screw with a special thread.

2. Description of the Related Art

In the art of orthopedic surgery, and particularly in spinal surgery, it has long been known to affix an elongated member, such as a plate or rod, to bones in order to hold them and support them in a given position. For example, in a procedure to fuse damaged, diseased, malformed or otherwise abnormal vertebrae, the vertebrae are positioned in a corrected position by a surgeon. An elongated plate is placed adjacent to the vertebral bone, and bone anchors, such as specially-configured screws or bolts, are employed to secure the plate to the bones. With such anchors placement is accomplished by drilling one or more holes in the bone(s), and threading the anchors into the holes. An anchor can be connected to the bone, as by threading into a vertebral hole, through a plate, or alternatively the plate can be placed in position over or around the anchor after the anchor is connected to the bone. The anchor and plate are then secured to each other to minimize or prevent relative movement. In this way, bones may be spinal held and/or supported in proper alignment for healing. However, since the vertebrae can move at multiple angles, forces at different directions or angles generated by the relative movement between the bones can push and turn the screws in the vertebral holes, and causing them to pull out.

Furthermore, the typical bone screw has the same thread rotation angle along its entire body; when force generated by the relative movement between the bones pushes the screw, or the tip end of the thread reaches the edge of the through hole of the bone plate, the screw can be easily pushed or turned.

Therefore, it is desirable to provide a bone fixation device to mitigate and/or obviate the aforementioned problems.

SUMMARY OF THE INVENTION

A main objective of the present invention is to provide a bone fixation device.

Another objective of the present invention is to provide a bone fixation device comprising a bone plate having a plurality of through holes and one or a plurality of bone screws; the bone plate further comprises a slide track and a plurality of sliding covers for covering the through holes on the bone plate.

Another objective of the present invention is to provide a bone fixation device comprising a bone plate having a plurality of through holes and one or a plurality of bone screws; the bone screw has a head portion, a neck portion and a threaded body. The thread of the bone screw starts at a conjunction between the neck portion and the threaded body, and the thread closest to the conjunction has an angle slightly inclined towards the threaded body or parallel with the conjunction.

Another objective of the present invention is to provide a bone fixation device that also comprises a plurality of fixed sunken spots on the slide track that can engage with a plurality of fixed raised spots on the slide cover. The bone fixation device comprises a bone plate having a plurality of through holes, and one or a plurality of bone screws. A slide track is mounted on a surface of the bone plate, and the bone plate further comprises one or a plurality of sliding covers having a plurality of hook tracks and side pieces. The hook tracks slidablely cover the slide track, and the side pieces are capable of covering the through holes.

The present invention provides another bone fixation device that comprises a bone plate having a plurality of through holes, and one or a plurality of bone screws. Each bone screw has a head portion, a neck portion and a threaded body. The neck portion is connected to the head portion and the threaded body. The thread of the bone screw starts at the conjunction between the neck portion and the threaded body, and the thread portion closest to the conjunction has an angle slightly inclined towards the threaded body or parallel with the conjunction.

In the bone fixation device, the slide track is an elongated raised track strip having two concave sides, and the two concave sides further comprise a plurality of fixed sunken spots.

In the bone fixation device, the hook tracks are two square U-shaped side walls facing each other, and have a plurality of fixed raised spots so that when the hook tracks slidablely cover the slide track the plurality of fixed raised spots moveably engage with the plurality of fixed sunken spots.

Furthermore, in the bone fixation device, the side pieces and the slide cover surfaces are fashioned as a single piece and extend in opposite directions.

In this invention, orientations, such as "raised", "concave" or "sunken", are based upon the centerline of the device.

Other objects, advantages, and novel features of the invention will become more apparent from the following detailed description when taken in conjunction with the accompanying drawings.

DETAILED DESCRIPTION OF THE PREFERRED EMBODIMENT

Figure 1A:
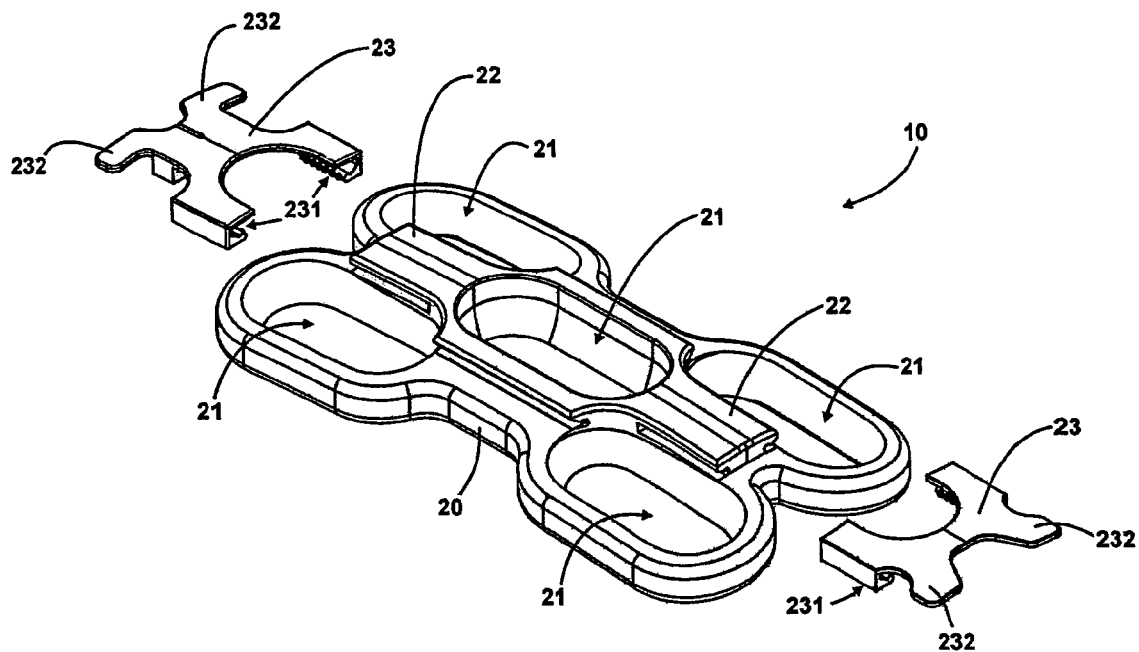
FIG. 1a and FIG. 1b are schematic drawings of a preferred embodiment of the present invention, showing a bone plate and one or a plurality of sliding covers.
Figure 1B:
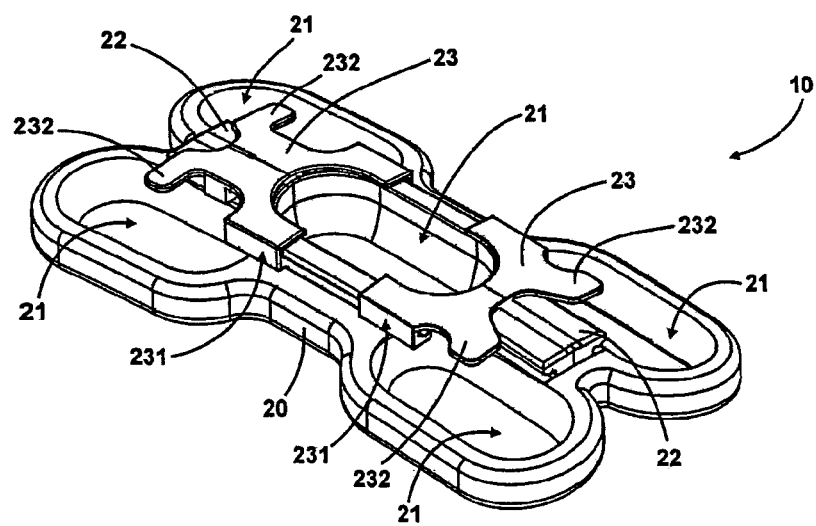

As shown in FIG. 1a and FIG. 1b, a bone fixation device 10 comprises a bone plate 20 for affixing to bone, a plurality of elongated through holes 21, a slide track 22 mounted on a surface of the bone plate 20, which is designed based on the position, shape and arrangement of the through holes 21, and one or a plurality of sliding covers 23, which have a plurality of hook tracks 231 and side pieces 232. The hook tracks 231 cover and slide on the slide track 22, and the side pieces 232 are also capable of sliding over and covering the through holes 21.

Figure 2A:
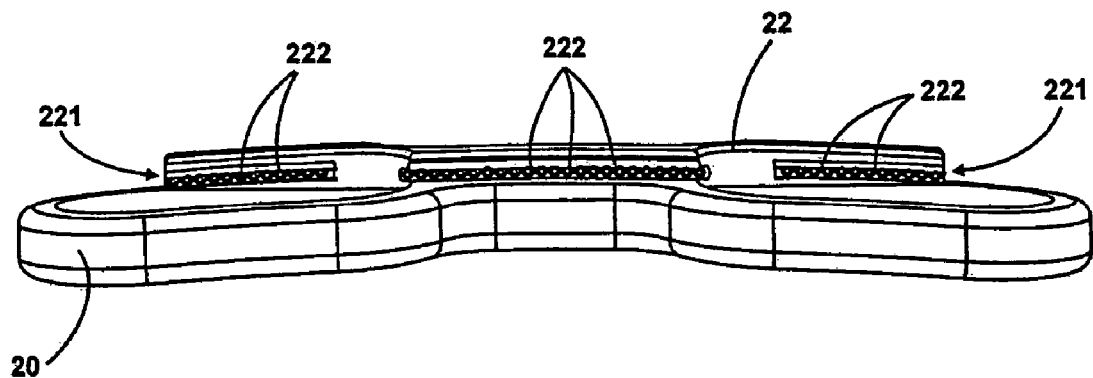
FIG. 2a and FIG. 2b are front view and side view drawings of the present invention.
Figure 2B:
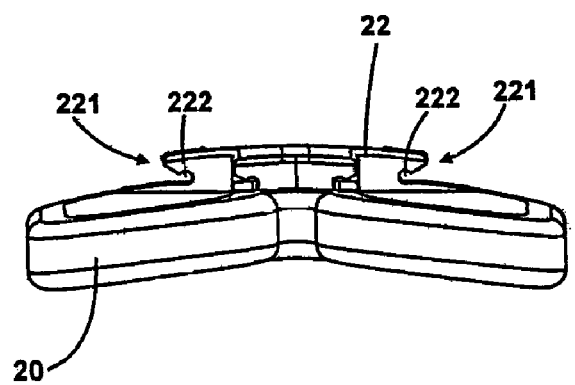

As shown in FIG. 2a and FIG. 2b, the slide track 22 mounted on the bone plate 20 is an elongated, raised track strip having two concave sides 221 with which the hook tracks 231 of the sliding covers 23 engage to prevent the sliding covers 23 from falling off, and the two concave sides 221 further comprise a plurality of fixed sunken spots 222.

Figure 3A:
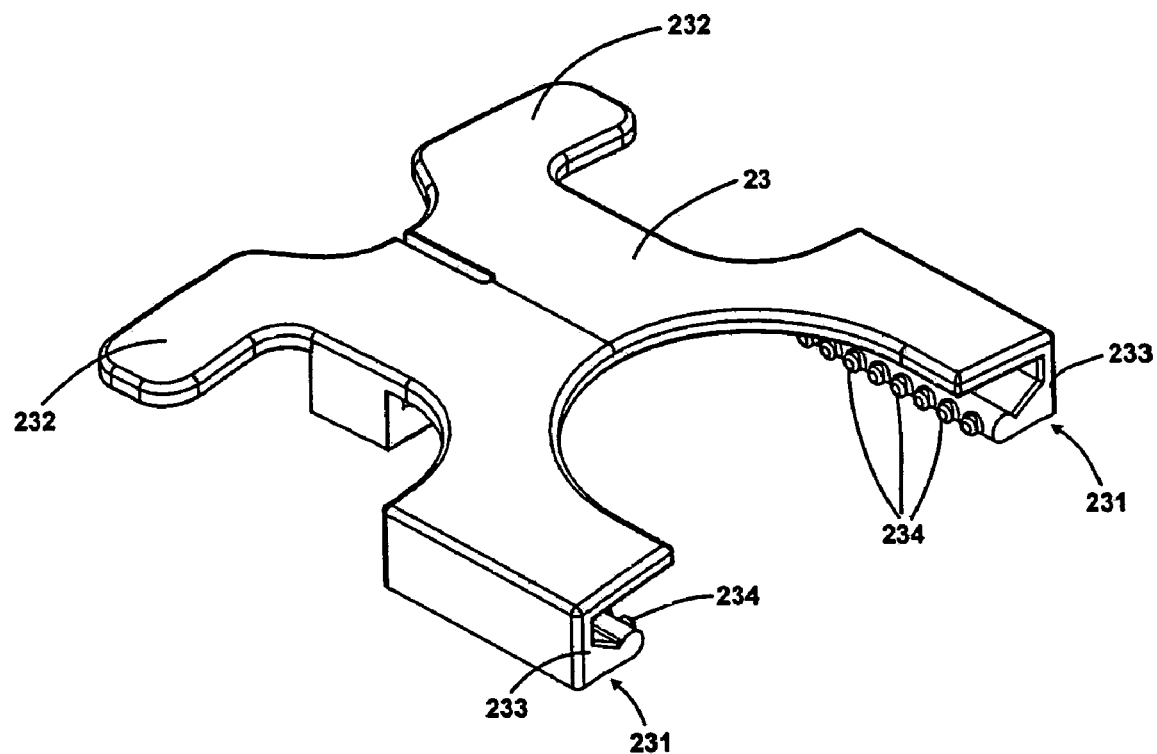
FIG. 3a and FIG. 3b are perspective view and front view drawings of the present invention.
Figure 3B:
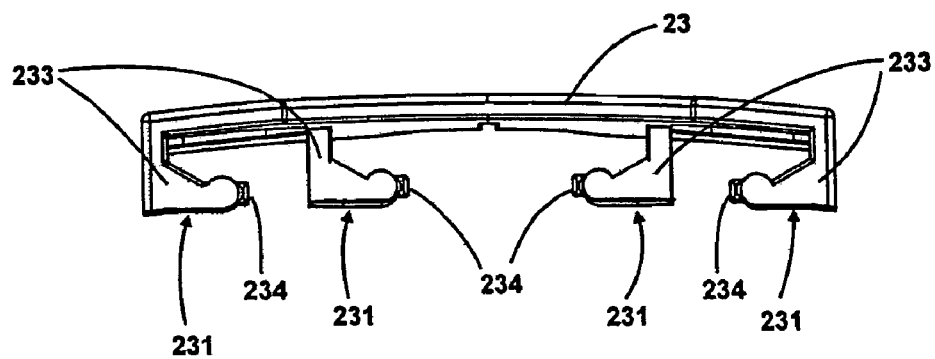

As shown in FIG. 3a and FIG. 3b, the hook tracks 231 of the sliding covers 23 are two square U-shaped and opposed square U-shaped side walls 233 that face each other, and have a plurality of fixed raised spots 234 so that when the hook tracks 231 slidablely cover the slide track 22 the plurality of fixed raised spots 234 moveably engage with the plurality of fixed sunken spots 222. The side pieces 232 and the slide cover surface are fashioned as a single piece and extend in opposite directions.

Figure 4A:
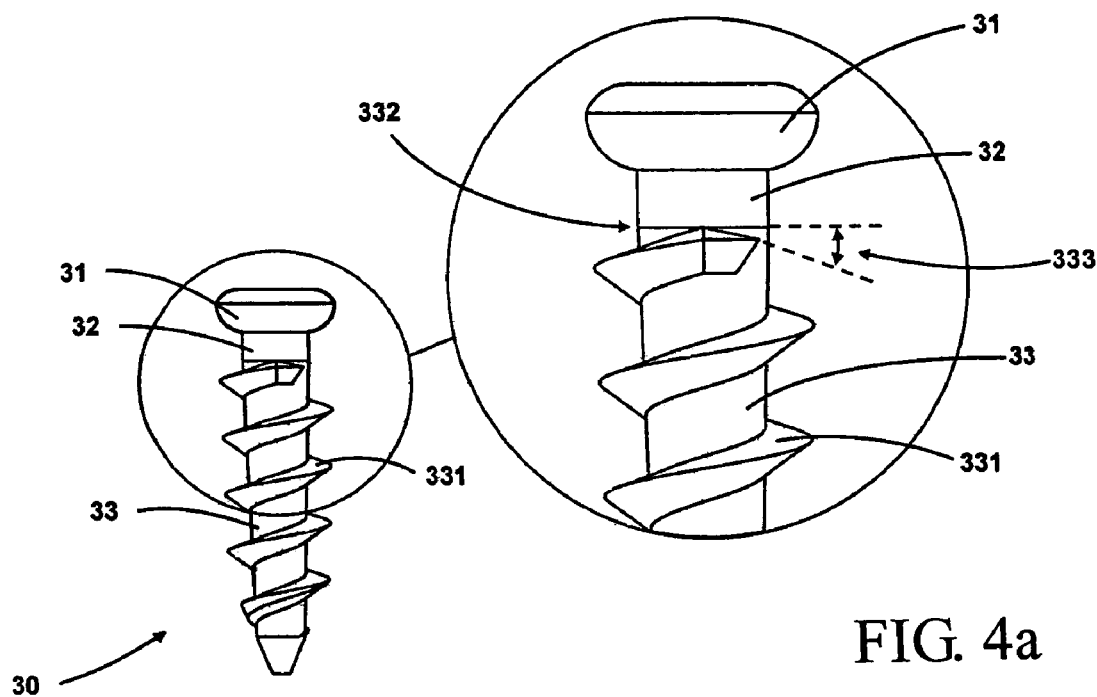
FIG. 4a and FIG. 4b are front view and side view drawings of a preferred embodiment of the present invention, showing one or a plurality of bone screws.
Figure 4B:
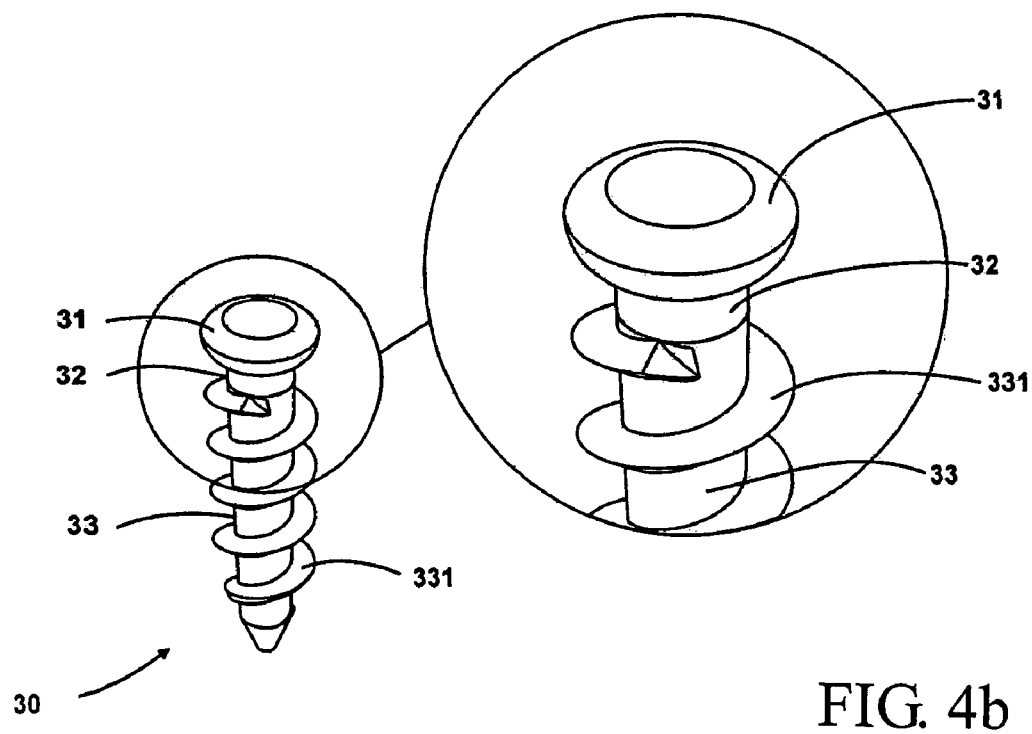

As shown in FIG. 4a and FIG. 4b, the bone fixation device 10 comprises one or a plurality of bone screws 30; the bone screws 30 have a head portion 31, a neck portion 32 and a threaded body 33. The neck portion 32 is connected to the head portion 31 and the threaded body 33 and has a predetermined length; a thread 331 of the bone screw 33 starts from a conjunction 332 between the neck portion 32 and the threaded body 33 to the end of the threaded body 33, and the thread 331 closest to the conjunction 332 has an angle slightly inclined towards the threaded body 33, or that is parallel with the conjunction 332. Therefore, when the bone screw 30 is implanted into bone tissue through the bone plate 20, the thread 331 will not be pushed and turned so that the bone screw 30 does not pull out.

Although the present invention has been explained in relation to its preferred embodiment, it is to be understood that many other possible modifications and variations can be made without departing from the spirit and scope of the invention as hereinafter claimed.

What is claimed is:

1. A bone fixation device comprising:
a bone plate having a plurality of through holes; and
one or a plurality of bone screws;
wherein the bone fixation device is characterized by a slide track formed on a surface of the bone plate, and the bone plate further comprises one or a plurality of sliding covers having a plurality of hook tracks and side pieces, the hook tracks slidably covering the slide track, and the side pieces capable of covering the through holes,
wherein the slide track is an elongated raised track strip having two concave sides, and the two concave sides further comprise a plurality of fixed sunken spots, and
wherein the hook tracks are two square U-shaped side walls facing each other, and have a plurality of fixed raised spots so that when the hook tracks slidably cover the slide track the plurality of fixed raised spots moveably engage with the plurality of fixed sunken spots.

2. The bone fixation device as claimed in claim 1, wherein the side pieces and the slide cover are fashioned as a single piece and extend in opposite directions.

3. The bone fixation device as claimed in claim 1, wherein the bone screw has a head portion, a neck portion and a threaded body, the neck portion connected to the head portion and the threaded body, a thread of the bone screw starting at a conjunction between the neck portion and the threaded body, and a thread close to the conjunction has an angle slightly inclined towards the threaded body or parallel with the conjunction.

* * * * *